US012788949B2

(12) United States Patent
Ushida et al.

(10) Patent No.: US 12,788,949 B2
(45) Date of Patent: Nov. 10, 2026

(54) GUIDE WIRE AND METHOD FOR MANUFACTURING GUIDE WIRE

(71) Applicant: Asahi Intecc Co., Ltd., Seto (JP)

(72) Inventors: Keisuke Ushida, Seto (JP); Naozumi Iwata, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 1255 days.

(21) Appl. No.: 17/678,089

(22) Filed: Feb. 23, 2022

(65) Prior Publication Data

US 2022/0176083 A1 Jun. 9, 2022

Related U.S. Application Data

(63) Continuation of application No. PCT/JP2019/034187, filed on Aug. 30, 2019.

(51) Int. Cl.
*A61M 25/09* (2006.01)
*A61M 25/02* (2006.01)

(52) U.S. Cl.
CPC .. *A61M 25/09016* (2013.01); *A61M 25/0905* (2013.01); *A61M 2025/0293* (2013.01); *A61M 2025/09083* (2013.01); *A61M 2025/09108* (2013.01); *A61M 2025/09133* (2013.01)

(58) Field of Classification Search
CPC ........ A61M 25/09016; A61M 25/0905; A61M 25/09; A61M 2025/0293; A61M 2025/09083; A61M 2025/09108; A61M 2025/09133
USPC .......................................................... 600/585
See application file for complete search history.

(56) References Cited

U.S. PATENT DOCUMENTS

| | | | | |
|---|---|---|---|---|
| 6,132,389 | A | 10/2000 | Cornish et al. | |
| 2005/0054950 | A1 | 3/2005 | Parins | |
| 2008/0281396 | A1 | 11/2008 | Ishida et al. | |
| 2010/0292613 | A1* | 11/2010 | Nowak, Jr. | A61M 25/09 600/585 |
| 2011/0015618 | A1 | 1/2011 | Satou et al. | |
| 2011/0160703 | A1 | 6/2011 | Matsumoto et al. | |
| 2013/0006149 | A1* | 1/2013 | Purtzer | A61M 25/09 600/585 |

(Continued)

FOREIGN PATENT DOCUMENTS

| | | | | |
|---|---|---|---|---|
| CN | 106535752 A | | 3/2017 | |
| EP | 2865406 A1 | * | 4/2015 | A61M 25/09 |

(Continued)

OTHER PUBLICATIONS

International Search Report and Written Opinion mailed on Oct. 8, 2019, received for PCT Application PCT/JP2019/034187, Filed on Aug. 30, 2019, 10 pages including English Translation.

*Primary Examiner* — Jacqueline Cheng
*Assistant Examiner* — Jonathan E. Cooper
(74) *Attorney, Agent, or Firm* — XSENSUS LLP

(57) ABSTRACT

A guide wire includes: a first core shaft made of a super-elastic material, and a second core shaft made of a material more plastically deformable than the first core shaft and is joined to a distal end portion of the first core shaft. On the distal end portion to which the second core shaft is joined in the first core shaft, breaking elongation attributed to a tensile load is shorter compared to portions on a proximal end side with respect to the distal end portion.

22 Claims, 16 Drawing Sheets

(56) References Cited

U.S. PATENT DOCUMENTS

| | | | | |
|---|---|---|---|---|
| 2013/0226033 | A1* | 8/2013 | Eskuri | A61M 25/09 600/585 |
| 2019/0097341 | A1* | 3/2019 | Endo | C25D 7/00 |
| 2021/0001092 | A1* | 1/2021 | Ishida | A61M 25/09 |

FOREIGN PATENT DOCUMENTS

| | | | | |
|---|---|---|---|---|
| EP | 3 171 764 | A1 | 5/2017 | |
| JP | 4-292174 | A | 10/1992 | |
| JP | 2006-519069 | A | 8/2006 | |
| JP | 2010-240201 | A | 10/2010 | |
| JP | 2011-130976 | A | 7/2011 | |
| JP | 2013-544575 | A | 12/2013 | |
| JP | 2015024019 | A * | 2/2015 | A61M 25/09 |
| WO | 95/19800 | A2 | 7/1995 | |
| WO | 2004/075967 | A1 | 9/2004 | |
| WO | 2008/139829 | A1 | 11/2008 | |
| WO | 2009/119386 | A1 | 10/2009 | |
| WO | 2012/058302 | A1 | 5/2012 | |
| WO | 2016/012902 | A1 | 1/2016 | |

* cited by examiner

GUIDE WIRE AND METHOD FOR MANUFACTURING GUIDE WIRE

CROSS-REFERENCE TO RELATED APPLICATION

The present application claims priority to international application PCT/JP2019/034187, filed Aug. 30, 2019, the entire disclosure of which is incorporated herein by reference.

TECHNICAL FIELD

The disclosed embodiments relate to a guide wire, and a method for manufacturing the guide wire.

BACKGROUND ART

There is known a guide wire used for inserting a catheter or the like into a blood vessel. In such a guide wire, to improve selectivity for blood vessels and smoothly lead the guide wire to a target site in the blood vessel, a shape such as a small curve is provided to a distal end portion of the guide wire in some cases. For example, Patent Literatures 1 to 5 disclose a guide wire in which a ribbon (shaping ribbon) made of stainless steel is joined to a distal end of a long shaft (wire main body) made of a nickel-titanium alloy to facilitate shaping of the distal end portion.

CITATION LIST

Patent Literature

Patent Literature 1: JP 2006-519069 W
Patent Literature 2: WO2009/119386
Patent Literature 3: JP 2013-544575 W
Patent Literature 4: JP 2010-240201 A
Patent Literature 5: JP H4-292174 A

SUMMARY OF THE INVENTION

Technical Problems

Herein, the long shaft and the ribbon are joined by soldering or brazing between the long shaft and the ribbon arranged adjacent to each other. Herein, the nickel-titanium alloy constituting the long shaft and the stainless steel constituting the ribbon significantly differ from each other in a strain amount leading to breaking. Thus, in the guide wires described in Patent Literatures 1 to 5 have had a problem that, when a load (e.g., tensile load) is applied to a joint part between the long shaft and the ribbon, the nickel-titanium alloy having a large strain amount is elongated, and the long shaft is detached from the joint part.

Such a problem is not limited to a vascular system, and is common to guide wires to be inserted into various organs in a human body, such as a lymphatic system, a biliary system, a urinary system, a respiratory system, a digestive system, a secretory gland, and a reproductive organ. In addition, such a problem is not limited to the guide wire including a long shaft made of a nickel-titanium alloy and a ribbon made of stainless steel, and is common to guide wires prepared by joining a plurality of core shafts made of materials that significantly differ from each other in the strain amount leading to breaking.

The disclosed embodiments have been made to solve the above problems, and to prevent detachment destruction on the joint part caused by applying a load to the guide wire including a plurality of core shafts joined together.

Solution to Problems

The disclosed embodiments were made to solve at least one or more of a part of the aforementioned problems, and can be achieved as the following aspects.

(1) According to one aspect of the disclosed embodiments, a guide wire is provided. The guide wire includes a first core shaft that is made of a superelastic material, and a second core shaft that is made of a material more plastically deformable than the first core shaft and is joined to a distal end portion of the first core shaft. On the distal end portion to which the second core shaft is joined in the first core shaft, a breaking elongation attributed to a tensile load is shorter compared to portions on a proximal end side with respect to the distal end portion. This "breaking elongation" is also referred to as a "strain amount" leading to breaking.

According to this configuration, on the distal end portion to which the second core shaft is joined in the first core shaft made of the superelastic material, the breaking elongation attributed to the tensile load is shorter compared to the portions on the proximal end side with respect to the distal end portion. Thereby, the elongation of the first core shaft can be prevented on the joint part, so that the interface detachment of the first core shaft from the joint part can be prevented. As a result, this configuration makes it possible to prevent the detachment destruction of the joint part caused by applying a tensile load to the guide wire including the jointed first and second core shafts.

(2) In the guide wire according to the above aspect, an amount of the breaking elongation attributed to the tensile load on the distal end portion of the first core shaft may be closer to an amount of a breaking elongation attributed to a tensile load on the second core shaft, compared to the portions on the proximal end side with respect to the distal end portion.

According to this configuration, on the distal end portion to which the second core shaft is joined in the first core shaft made of the superelastic material, an amount of the breaking elongation attributed to the tensile load can be closer to an amount of the breaking elongation attributed to the tensile load on the second core shaft compared to the portions on the proximal end side with respect to the distal end portion, so that the interface detachment of the first core shaft from the joint part between the first core shaft and the second core shaft can be prevented.

(3) In the guide wire according to the above aspects, a nanoindentation hardness on the distal end portion of the first core shaft may be higher compared to the portions on the proximal end side with respect to the distal end portion.

According to this configuration, on the distal end portion to which the second core shaft is joined in the first core shaft made of the superelastic material, the nanoindentation hardness is higher compared to the portions on the proximal end side with respect to the distal end portion. That means, according to this configuration, a superelasticity of the superelastic material can be eliminated or reduced on the distal end portion to which the second core shaft is joined in the first core shaft. Thereby, the elongation of the first core shaft can be prevented on the joint part, so that the interface detachment of the first core shaft from the joint part can be prevented.

(4) In the guide wire according to the above aspects, the nanoindentation hardness on the distal end portion of the first core shaft may be not equal to or greater than 1.1 times the nanoindentation hardness of the portions on the proximal end side with respect to the distal end portion.

According to this configuration, when the nanoindentation hardness on the distal end portion of the first core shaft is equal to or greater than 1.1 times the nanoindentation hardness of the portions on the proximal end side with respect to the distal end portion, the superelasticity of the superelastic material can be eliminated or reduced.

(5) In the guide wire according to the above aspects, the nanoindentation hardness on the distal end portion of the first core shaft may be 4500 N/mm$^2$ or higher.

According to this configuration, when the nanoindentation hardness on the distal end portion of the first core shaft is 4500 N/mm$^2$ or higher, the superelasticity of the superelastic material can be eliminated or reduced in a way that.

(6) In the guide wire according to the above aspects, the first core shaft further has a reduced diameter portion whose outer diameter decreases from the proximal end side toward the distal end side, wherein the distal end portion of the first core shaft may be connected to a distal end of the reduced diameter portion.

According to this configuration, since the first core shaft further has the reduced diameter portion whose outer diameter decreases from the proximal end side toward the distal end side, a rigidity of the first core shaft can be gradually changed on the reduced diameter portion. As a result, it is possible to provide a guide wire whose flexibility gradually increases from the proximal end side toward the distal end side.

(7) In the guide wire according to the above aspects, a gradually-changed portion whose nanoindentation hardness gradually increases from the proximal end side toward the distal end side may be disposed on the distal end portion of the reduced diameter portion. According to this configuration, the gradually-changed portion whose nanoindentation hardness gradually increases from the proximal end side toward the distal end side is disposed on the distal end portion of the reduced diameter portion. Thereby, the superelasticity of the first core shaft can be gradually decreased on the gradually-changed portion.

(8) According to one aspect of the disclosed embodiments, a method for manufacturing a guide wire is provided. This manufacturing method includes: subjecting a distal end portion of a first core shaft made of a superelastic material, to first processing using at least one method of pressing, swaging, and drawing; and joining a second core shaft made of a material that is more plastically deformable than the first core shaft, to the distal end portion subjected to the first processing.

According to this configuration, the method for manufacturing the guide wire includes processing the distal end portion of the first core shaft made of the superelastic material, using at least one method of pressing, swaging, and drawing. Thus, on the distal end portion of the first core shaft, a breaking elongation can be easily be shortened and a nanoindentation hardness can be easily increased compared to the portions on the proximal end side with respect to the distal end portion by pressing, swaging, or drawing. In addition, an amount of the breaking elongation on the distal end portion of the first core shaft can be closer to an amount of the breaking elongation attributed to a tensile load on the second core shaft, compared to the portions on the proximal end side with respect to the distal end portion.

Note that the disclosed embodiments can be achieved in various aspects, e.g., in a form of a core shaft product composed of a plurality of core shafts used for a guide wire, a method for manufacturing the guide wire, or the like.

DETAILED DESCRIPTION

First Embodiment

Figure 1:
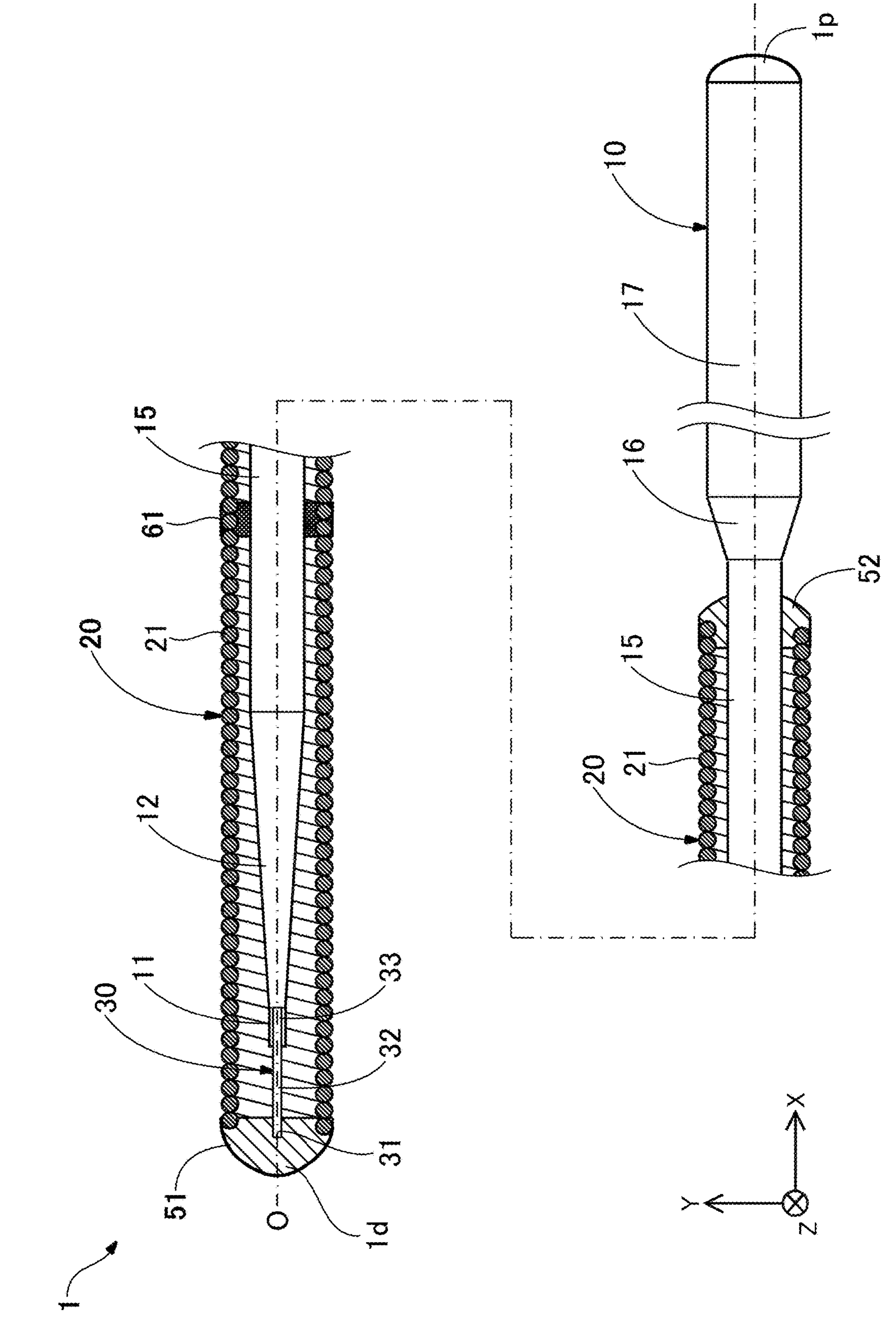
FIG. 1 illustrates a configuration of a guide wire according to the first embodiment.

FIG. 1 illustrates a configuration of a guide wire 1 according to the first embodiment. The guide wire 1 is, e.g., a medical appliance used for inserting a medical device, such as a catheter, into a living body lumen, such as, a blood vessel. The guide wire 1 may include a first core shaft 10, a coil body 20, a second core shaft 30, a distal fixation portion 51, a proximal fixation portion 52, and an intermediate fixation portion 61. In the guide wire 1 according to the first embodiment, a distal end portion of the first core shaft 10 to which the second core shaft 30 is joined prevents interface detachment of the first core shaft from a joint part between the first core shaft 10 and the second core shaft 30 compared to the portions on the proximal end side with respect to the distal end portion, by having a correlation shown in Table 1.

TABLE 1

| | Distal end portion | Proximal end side |
|---|---|---|
| Amount of breaking elongation (strain amount) | Small | Large |
| Nanoindentation hardness | High | Low |

In FIG. 1, a central axis of the guide wire 1 is represented by an axis line O (dot and dash line). In the following examples, a central axis of the first core shaft 10 on the proximal end side with respect to a first large diameter portion 15 and a central axis of the coil body 20 both coincide with the axis line O. However, each of the central axis of the first core shaft 10 and the central axis of the coil body 20 may be inconsistent with the axis line O. FIG. 1 illustrates XYZ-axes orthogonal to each other. The X-axis corresponds to a length direction of the guide wire 1, the Y-axis corresponds to a height direction of the guide wire 1, and the Z-axis corresponds to a width direction of the guide wire 1. In FIG. 1, the left side (−X-axis direction) is referred to as a "distal end side" of the guide wire 1 and each component, and the right side (+X-axis direction) is referred to as a "proximal end side" of the guide wire 1 and each component. As for the guide wire 1 and each component, an end portion positioned on the distal end side is referred to as a "distal end", and the distal end and the vicinity thereof are referred to as a "distal end portion". In addition, an end portion positioned on the proximal end side is referred to as a "proximal end", and the proximal end and the vicinity thereof are referred to as a "proximal end portion". The distal end side corresponds to a "far side" to be inserted into a living body, and the proximal end side corresponds to a "near side" to be operated by an operator such as a surgeon. These definitions are common for the figures following FIG. 1.

The first core shaft 10 is a tapered long member having a large diameter on the proximal end side and a small diameter on the distal end side. The first core shaft 10 is made of a superelastic material, e.g., a NiTi (nickel-titanium) alloy, or an alloy of NiTi and another metal. The first core shaft 10 has a distal end portion 11, a first reduced diameter portion 12, e.g., a first variable diameter portion, a first large diameter portion 15, a second reduced diameter portion 16, e.g., a second variable diameter portion, and a second large diameter portion 17, in this order from the distal end side to the proximal end side. In particular, the first reduced diameter portion 12 may have a diameter that increases, e.g., continuously, from a diameter of the distal end portion 11 to a diameter of the first large diameter portion 15, and the second reduced diameter portion 16 may have a diameter that increases, e.g., continuously, from a diameter of the first large diameter portion 15 to a diameter of the second large diameter portion 17. An outer diameter and a length of each portion can be arbitrarily determined. The first core shaft 10 may be made of a pseudoelastic NiTi alloy or the like.

Figure 2:
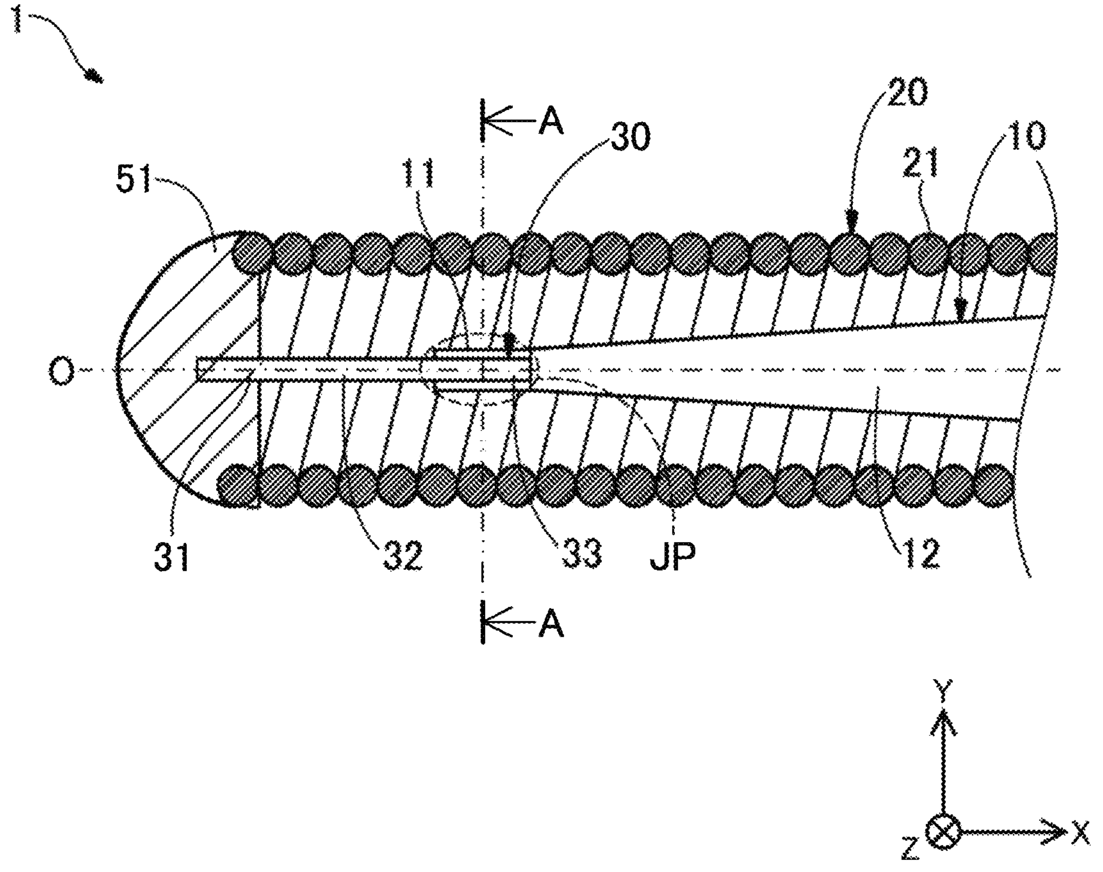
FIG. 2 is illustrates a configuration of a distal end side of the guide wire.
Figure 3:
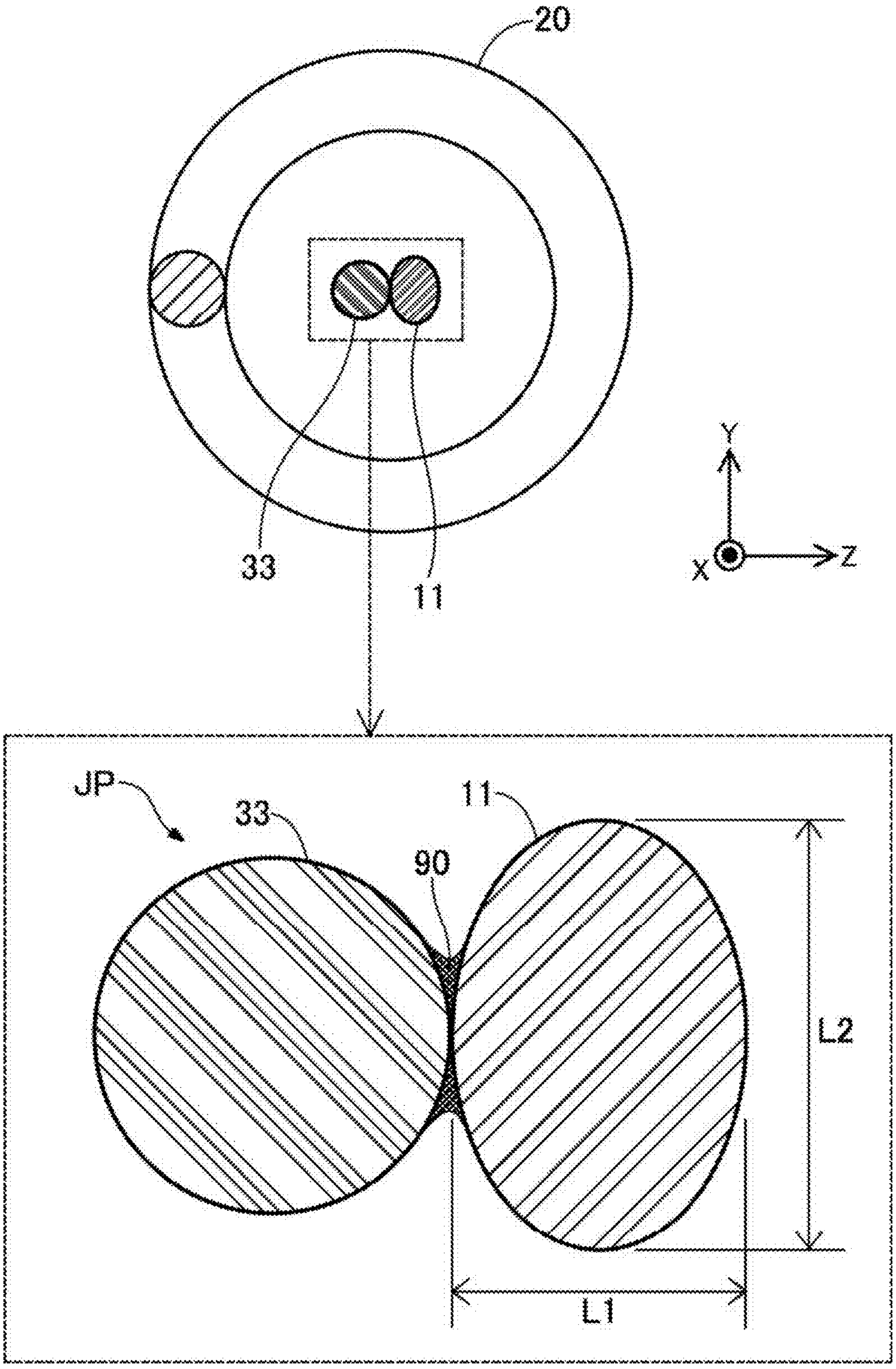
FIG. 3 is a sectional view taken along line A-A (FIG. 2) of the guide wire.

FIG. 2 illustrates a configuration of the distal end side of the guide wire 1. FIG. 3 is a sectional view taken along line A-A (FIG. 2) of the guide wire 1. In FIG. 3, a sectional view taken along line A-A is illustrated in the upper part, and a partial enlarged view illustrating a vicinity of a part where the first core shaft 10 and the second core shaft 30 are joined (hereinafter also referred to as a "joint part JP") is illustrated in the lower part.

The distal end portion 11 is disposed on the distal end side of the first core shaft 10 and is a part to which the second core shaft 30 described later is joined. The distal end portion 11 has the smallest transverse sectional area compared to those of the other portions (first reduced diameter portion 12, first large diameter portion 15, etc.) of the first core shaft 10. The distal end portion 11 has an almost elliptical transverse section as illustrated in FIG. 3. The distal end portion 11 is arranged such that a short side L1 is positioned in a direction flanked by the second core shaft 30 (Z-axis direction in the example of FIG. 3), as illustrated in the lower part of FIG. 3. In other words, the width L1 of the distal end portion 11 is shorter than a height L2 in the illustrated transverse section. Specific values of the width L1 and height L2 can be arbitrarily determined.

The first reduced diameter portion 12 is disposed between the distal end portion 11 and the first large diameter portion 15. The first reduced diameter portion 12 has an almost truncated cone shape with an outer diameter decreasing from the proximal end side toward the distal end side. The first large diameter portion 15 is disposed between the first reduced diameter portion 12 and the second reduced diameter portion 16. The first large diameter portion 15 has an almost cylindrical shape with a substantially constant outer diameter larger than the height L2 of the distal end portion 11. The second reduced diameter portion 16 is disposed between the first large diameter portion 15 and the second large diameter portion 17. The second reduced diameter portion 16 has an almost truncated cone shape with an outer diameter decreasing from the proximal end side toward the distal end side. The second large diameter portion 17 is disposed on the proximal end side of the first core shaft 10. The second large diameter portion 17 has an almost cylindrical shape with a substantially constant outer diameter larger than the other portions (second reduced diameter portion 16, first large diameter portion 15, etc.) of the first core shaft 10.

In the first core shaft 10 according to the first embodiment, a breaking elongation of the distal end portion 11 is shorter compared to the portions (i.e., first reduced diameter portion 12, first large diameter portion 15, second reduced diameter portion 16, and second large diameter portion 17) on the proximal end side with respect to the distal end portion 11. A correlation on the distal end portion 11 is closer to the correlation shown in Table 1, compared to the portions on the proximal end side with respect to the distal end portion 11.

As an example, in a first core shaft composed of a superelastic NiTi, a nanoindentation hardness of the distal end portion 11 according to the first embodiment is 4500 $N/mm^2$, and the nanoindentation hardness of the first reduced diameter portion 12, the first large diameter portion 15, the second reduced diameter portion 16, and the second large diameter portion 17 is each 4000 $N/mm^2$. In other words, the nanoindentation hardness of the distal end portion 11 is not less than 1.1 times the nanoindentation hardness of the portions on the proximal end side with respect to the distal end portion 11. The method for measuring the hardness is described later in FIG. 7. As another example, in a first core shaft composed of a pseudoelastic NiTi, a nanoindentation hardness of the distal end portion 11 is higher than 4500 $N/mm^2$, and the nanoindentation hardness of the first reduced diameter portion 12, the first large diameter portion 15, the second reduced diameter portion 16, and the second large diameter portion 17 positioned on the proximal end portion with respect to the distal end portion 11 is each higher than 4000 $N/mm^2$. That means, although the specific nanoindentation hardness value varies depending on a material property of the first core shaft, the relationship that the nanoindentation hardness of the distal end portion 11 is higher than the nanoindentation hardness of the portions on the proximal end side with respect to the distal end portion 11 does not vary.

Outer faces of the distal end portion 11, the first reduced diameter portion 12, and the first large diameter portion 15 may be covered with the coil body 20 described below. On the other hand, the second reduced diameter portion 16 and the second large diameter portion 17 may not be covered with the coil body 20 and are exposed from the coil body 20. An operator uses the second large diameter portion 17 for gripping the guide wire 1.

The coil body 20 may have an almost hollow cylindrical shape formed by spirally winding a wire 21 around the first core shaft 10 and the second core shaft 30. The coil body 20 may be a single-thread coil formed by winding one wire in a single-thread pattern, a multi-thread coil formed by winding a plurality of wires in a multi-thread pattern, a single-thread strand coil formed by winding, in a single-thread pattern, a strand composed of a plurality of wires twisted together, or a multi-thread strand coil formed by winding, in a multi-thread pattern, a plurality of strands composed of a plurality of wires twisted together. For the coil body 20, a wire diameter of the wire 21 and an average diameter of the coil (an average diameter of the outer diameter and inner diameter of the coil body 20) can be arbitrarily determined.

The wire 21 can be made of, for example, a stainless steel alloy such as SUS304 and SUS316, a superelastic alloy such as NiTi alloy, a piano wire, a radiolucent alloy such as nickel-chromium alloy and cobalt alloy, gold, platinum, tungsten, or a radiopaque alloy such as an alloy containing any of these elements (e.g. a platinum-nickel alloy). The wire 21 may be formed of a known material other than the above materials.

The second core shaft 30 may be a long member extending from the proximal end side toward the distal end side. The second core shaft 30 is made of a material that is more plastically deformable than the first core shaft 10, e.g., a stainless steel alloy such as SUS304 and SUS316. The second core shaft 30 is also referred to as "ribbon". The second core shaft 30 has a distal end portion 31, an intermediate portion 32, and a proximal end portion 33 in this order from the distal end side to the proximal end side. An outer diameter and a length of each portion can be arbitrarily determined.

The distal end portion 31 is disposed on the distal end side of the second core shaft 30 and is fixed by the distal fixation portion 51. The intermediate portion 32 is positioned between the distal end portion 31 and the proximal end portion 33 of the second core shaft 30. The proximal end portion 33 is disposed on the proximal end side of the second core shaft 30 and is joined to the first core shaft 10.

Similarly to the distal end portion 11 of the first core shaft 10, the second core shaft 30 may have a flat shape with an almost elliptical transverse section, and the transverse sectional shape is not particularly limited.

As illustrated in FIG. 3, the distal end portion 11 of the first core shaft 10 and the proximal end portion 33 of the second core shaft 30 are disposed adjacent to and joined to each other. As illustrated in the lower part of FIG. 3, this joining can be carried out in a way that a gap between the distal end portion 11 and the proximal end portion 33 arranged adjacent to each other is filled and solidified with a joining agent 90. The joining agent 90 may be, e.g., a metal solder such as silver solder, gold solder, zinc, Sn—Ag alloy, Au—Sn alloy, and the like, an adhesive such as an epoxy adhesive and the like may be used. The distal end portion 11 of the first core shaft 10 and the proximal end portion 33 of the second core shaft 30 may be joined by welding or another means. The joining way is not limited. Herein, the first core shaft 10 is arranged such that a longitudinal lateral side (height L2 direction) of the flat distal end portion 11 is adjacent to the second core shaft 30. Thereby, an area of a part where the first core shaft 10 and the second core shaft 30 are adjacent to each other can be enlarged, so that a joining strength between the first core shaft 10 and the second core shaft 30 can be improved.

As illustrated in FIG. 2, the distal end portion 11 of the first core shaft 10 and the proximal end portion 33 of the second core shaft 30 are joined such that their proximal ends coincide with each other in the axis line O direction. However, both positions of the proximal end of the distal end portion 11 and the proximal end of the proximal end portion 33 in the axis line O direction may be different. For example, the proximal end of the distal end portion 11 may be positioned in the ±X-axis direction from the proximal end of the proximal end portion 33. In addition, for example, the first core shaft 10 may be configured to be arranged such that a transverse-direction lateral face (width L1 direction) of the flat distal end portion 11 is adjacent to the second core shaft 30, and to be joined to the second core shaft 30.

The distal fixation portion 51 is positioned on the distal end portion of the guide wire 1 and integrally holds the distal end portion 31 of the second core shaft 30 and the distal end portion of the coil body 20. The distal fixation portion 51 can be made of any joining agent, e.g., a metal solder such as silver solder, gold solder, zinc, Sn—Ag alloy, Au—Sn alloy, and the like, or an adhesive such as an epoxy adhesive and the like. The proximal fixation portion 52 is disposed on the proximal end portion of the first large diameter portion 15 of the first core shaft 10, and integrally holds the first core shaft 10 and the proximal end portion of the coil body 20. The proximal fixation portion 52 can be made of any joining agent, similarly to the distal fixation portion 51. A joining agent used for the proximal fixation portion 52 and a joining agent used for the distal fixation portion 51 may be the same or different.

The intermediate fixation portion 61 integrally holds the coil body 20 and the first core shaft 10 in the vicinity of an intermediate portion of the coil body 20 in the axis line O direction. The intermediate fixation portion 61 can be made of any joining agent, similarly to the distal fixation portion 51. A joining agent used for the intermediate fixation portion 61 and a joining agent used for the distal fixation portion 51 may be the same or different. Although the one intermediate fixation portion 61 was illustrated in FIG. 1, the guide wire 1 may include a plurality of intermediate fixation portions 61. Alternatively, the guide wire 1 does not necessarily have the intermediate fixation portion 61.

This guide wire 1 can be manufactured as described below, for example. First, the first core shaft 10 made of a superelastic material and the second core shaft 30 made of a material that is more plastically deformable than the first core shaft 10 are prepared. The first core shaft 10 has an almost cylindrical (i.e., unflat) distal end portion 11 having a substantially constant outer diameter. Next, the distal end portion 11 of the first core shaft 10 is pressed to prepare the first core shaft 10 having the distal end portion 11 with a shorter breaking elongation compared to the proximal end portion of the first core shaft. Specifically, the distal end portion 11 of the first core shaft 10 has at least one of the properties of the flat shape, the short breaking elongation, and the high nanoindentation hardness explained in FIG. 1 to FIG. 3. Then, the proximal end portion 33 of the second core shaft 30 is joined to the distal end portion 11 of the first core shaft 10. Subsequently, the coil body 20 is arranged so as to cover the first and second core shafts 10 and 30. Finally, the distal fixation portion 51, the proximal fixation portion 52, and the intermediate fixation portion 61 are formed.

<Example of Effect>

As described above, in the guide wire 1 according to the first embodiment, the distal end portion 11 to which the second core shaft 30 is joined in the first core shaft 10 made of a superelastic material has a shorter breaking elongation attributed to the tensile load compared to the portions (first reduced diameter portion 12, first large diameter portion 15, second reduced diameter portion 16, and second large diameter portion 17) on the proximal end side with respect to the distal end portion. Thereby, the elongation of the first core shaft 10 can be prevented on the joint part JP, so that the interface detachment of the first core shaft 10 from the joint part JP can be prevented. As a result, according to the first embodiment, the detachment destruction of the joint part JP caused by applying a tensile load to the guide wire 1 including the jointed first and second core shafts 10 and 30 may be prevented.

In the guide wire 1 according to the first embodiment, on the distal end portion 11 to which the second core shaft 30 is joined in the first core shaft 10 made of a superelastic material, an amount of the breaking elongation attributed to the tensile load is closer to an amount of the breaking elongation attributed to the tensile load on the second core shaft 30, compared to the portions on the proximal end side with respect to the distal end portion 11. Thereby, the difference in the amount of the elongation between the first core shaft 10 and the second core shaft 30 on the joint part JP can be reduced, so that the interface detachment of the first core shaft 10 from the joint part JP can be prevented.

In the guide wire 1 according to the first embodiment, the distal end portion 11 to which the second core shaft 30 is joined in the first core shaft 10 made of a superelastic material has a higher nanoindentation hardness compared to the portions on the proximal end side with respect to the distal end portion 11. That means, according to the first embodiment, a superelasticity of the superelastic material can be eliminated or reduced on the distal end portion 11 to which the second core shaft 30 is joined in the first core shaft 10. Thereby, the "elongation" of the first core shaft 10 on the joint part JP due to the superelasticity can be reduced, and the interface detachment of the first core shaft 10 from the joint part JP can be prevented.

In the guide wire 1 according to the first embodiment, since the first core shaft 10 further has the first reduced diameter portion 12 whose outer diameter decreases from the proximal end side toward the distal end side, a rigidity of the first core shaft 10 can be gradually changed on the first reduced diameter portion 12. As a result, it is possible to provide the guide wire 1 whose flexibility gradually increases from the proximal end side toward the distal end side. Furthermore, the method for manufacturing the guide wire 1 includes pressing the distal end portion 11 of the first core shaft 10 made of a superelastic material. Thus, on the distal end portion 11 of the first core shaft 10, the breaking elongation attributed to the tensile load can be easily decreased and the nanoindentation hardness can be easily increased compared to the portions on the proximal end side with respect to the distal end portion 11, by pressing. In addition, on the distal end portion 11 of the first core shaft 10, the amount of the breaking elongation attributed to the tensile load can be closer to the amount of the breaking elongation attributed to the tensile load on the second core shaft 30, compared to the portions on the proximal end side with respect to the distal end portion 11.

<Test Result>

Withe reference to FIG. 4 to FIG. 6, it will be explained that the guide wire 1 according to the first embodiment can eliminate or reduce the superelasticity on the distal end portion 11 of the first core shaft 10. First, a tensile test was conducted for four first core shaft samples including the first core shaft with the configuration according to the first embodiment. In this tensile test, the "elongation" caused by the superelasticity of the first core shaft is quantitatively measured when a load is applied to the first core shaft.

Figure 4:
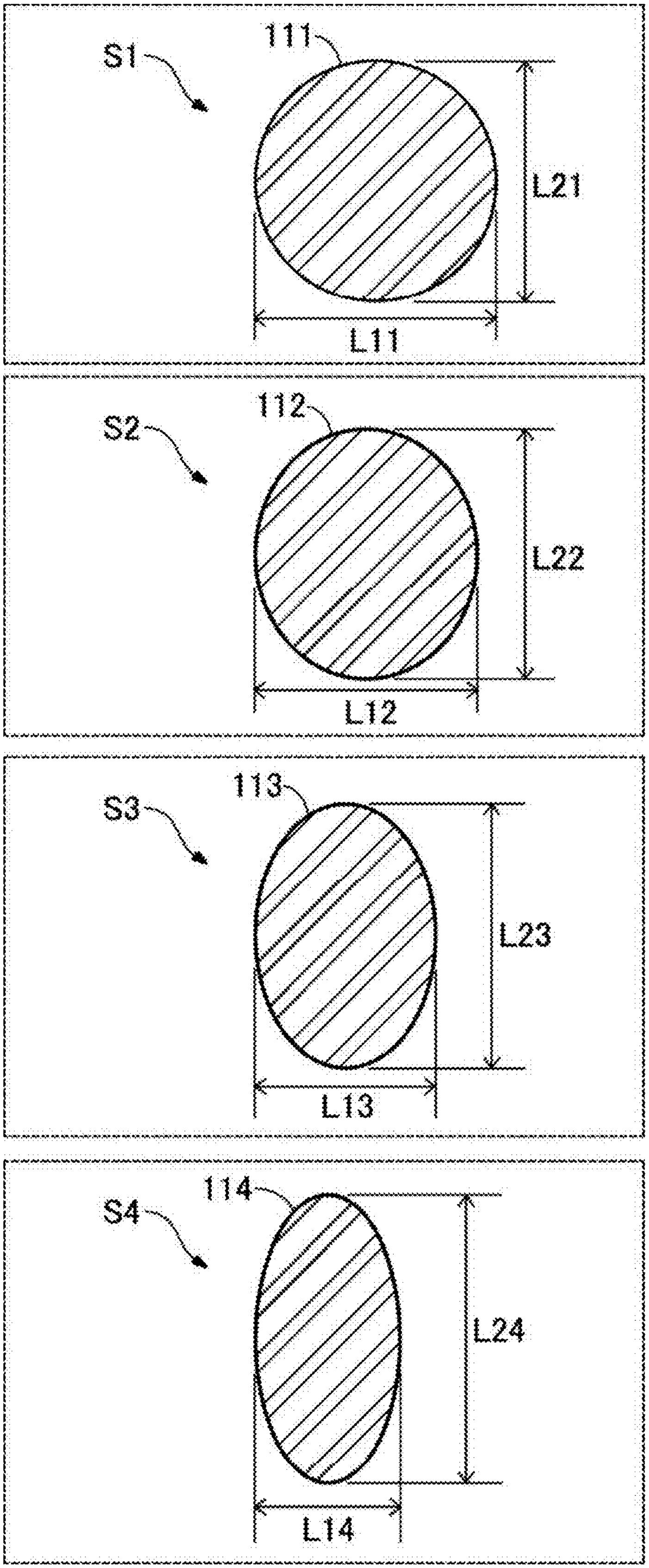
FIG. 4 illustrates configurations of samples of a first core shaft used in a tensile test.

FIG. 4 illustrates configurations of samples of the first core shaft used in the tensile test. FIG. 4 illustrates transverse sections of the distal end portions of the samples. Transverse sectional areas of the samples are all equal. A sample S1 of the first core shaft has a distal end portion 111 not subjected to the pressing. The distal end portion 111 has an almost circular transverse section, in which a width L11 and a height L21 are substantially equal. A sample S2 of the first core shaft has a distal end portion 112 subjected to the pressing. The distal end portion 112 has an almost elliptical transverse section, and 8% of processing rate. The processing rate is determined according to the following equation (1). Note that, in a case of height L22<width L12, the "width L12/height L22" in the following equation (1) is replaced by "height L22/width L12".

$$\text{Processing rate}=1\cdot(\text{width } L12/\text{height } L22)\times 100 \quad (1)$$

A sample S3 of the first core shaft is pressed to have a distal end portion 113 that is flatter than the sample S2. The distal end portion 113 has an almost elliptical transverse section, and 25% of processing rate. Similar to the sample S2, the processing rate is determined using the above equation (1). A sample S4 of the first core shaft is pressed to have a distal end portion 114 that is flatter than the sample S3. The distal end portion 114 has an almost elliptical transverse section, and 40% of processing rate. Similar to the sample S2, the processing rate is determined using the above equation (1).

Figure 5:
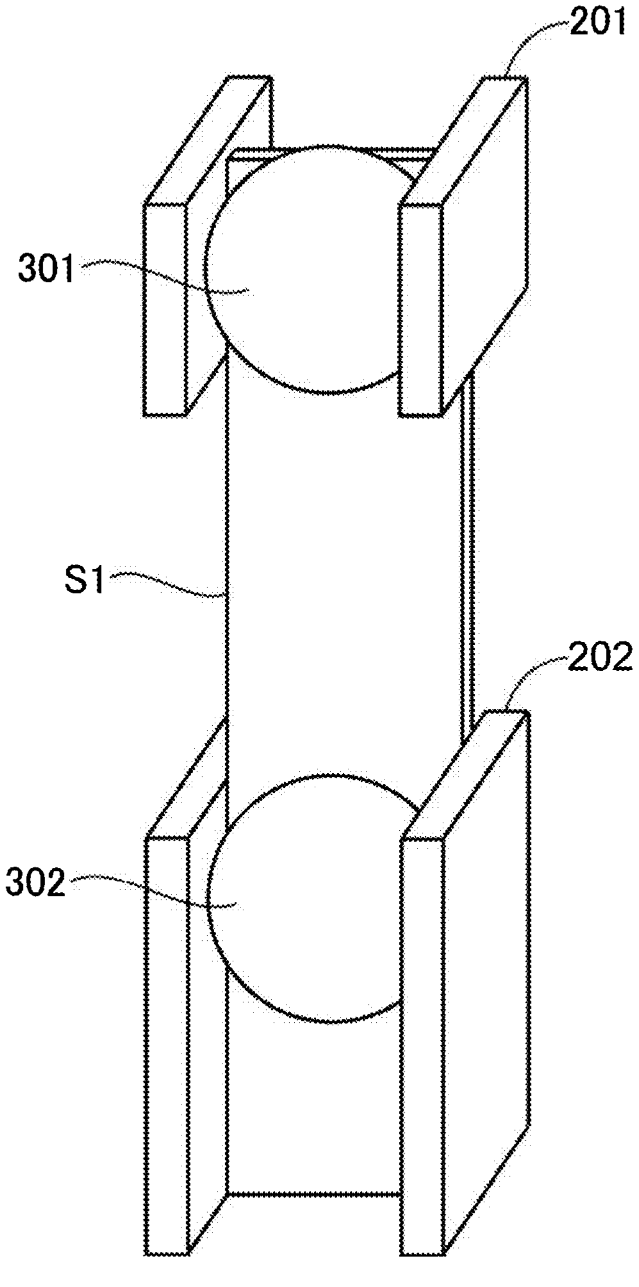
FIG. 5 illustrates a test method for the tensile test.

FIG. 5 illustrates a test method for the tensile test. In FIG. 5 and the following description, the sample S1 will be illustrated and explained. In the tensile test, a first chuck 201 and a second chuck 202 that are arranged apart from each other are used. First, a distal end portion of the sample S1 is fixed to the first chuck 201 by a solder agent 301, and an almost middle portion of the sample S1 is fixed to the second chuck 202 by a solder agent 302. In this state, the second chuck 202 was pulled downward in the vertical direction (direction apart from the first chuck 201), and a tensile load (N) and a strain (%) of the sample S1 were measured. The tensile test was continued until the sample S1 was broken. In this test, a length (span) between centers of the solder agents 301 and 302 was set to 15 mm, and a tensile speed was set to 5 mm/min. The samples S2 to S4 explained in FIG. 4 were also tested in the same way and under the same conditions as for the sample S1.

Figure 6:
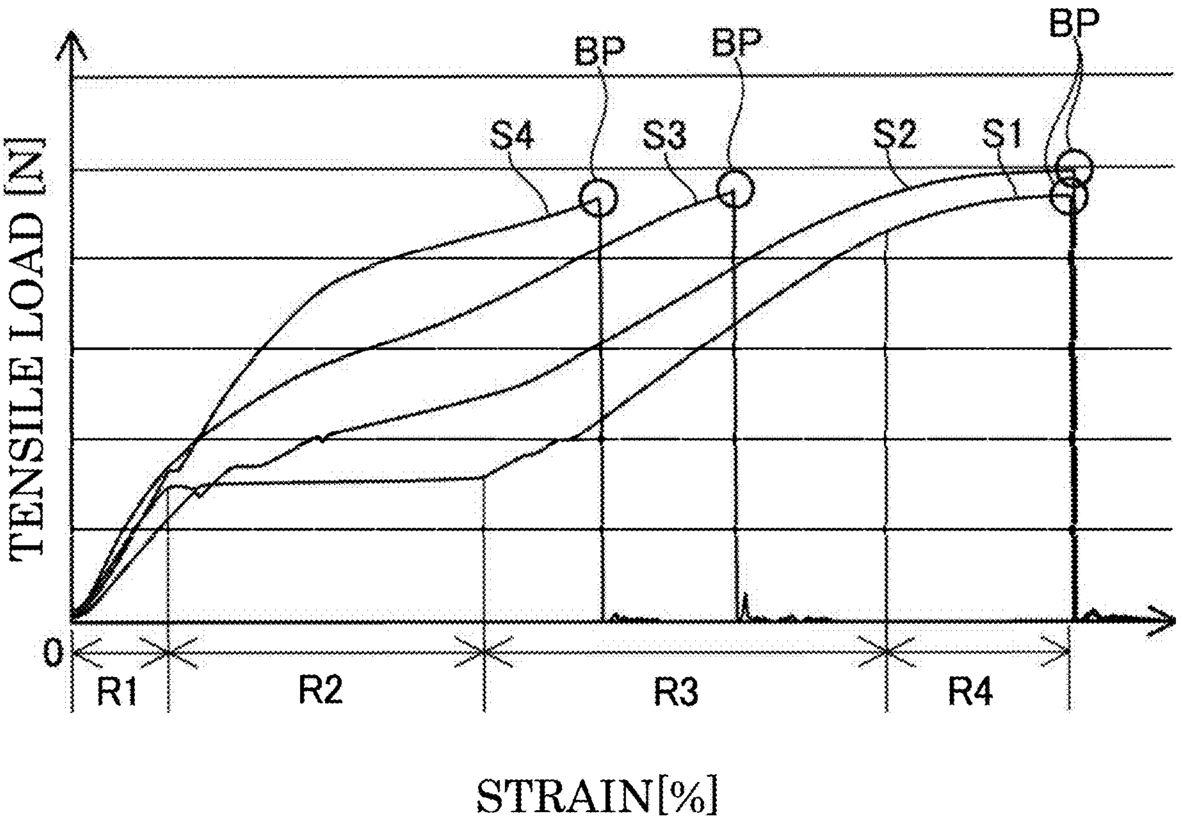
FIG. 6 illustrates results of the tensile test.

FIG. 6 illustrates results of the tensile test. FIG. 6 presents test results of the samples S1 to S4, in which the tensile loads (N) are plotted on the ordinate, and the strains (%) are plotted on the abscissa. As illustrated in the figure, in the sample S1 not subjected to the pressing, first, the strain increases in proportion to the increase in the tensile load (region R1: austenitic phase elastic region). Then, in the sample S1, the strain is maintained at a substantially constant level even when the tensile load increases (region R2: austenitic-martensitic phase transformation, plateau region), the strain increases slowly in proportion to the increase in the tensile load (region R3: martensitic phase elastic region), the strain increases even more slowly in proportion to the increase in the tensile load (region RA: martensitic phase compositional region), and the sample is broken at a point BP. Thus, the sample S1 without pressing has a so-called "superelasticity" characterized in that the plateau region R2 where the strain is maintained at a substantially constant level even when the tensile load increases is present between the superelastic region R1 and the plastic regions R3 and RA. Hereinafter, the strain leading to the breaking point BP is also referred to as the "breaking elongation".

Although the plateau region R2 substantially disappeared in the sample S2 with 8% processing rate, the results for the amount of increase in the strain attributed to the tensile load and the strain leading to the breaking point BP (breaking elongation) were similar to those in the sample S1 without pressing. On the other hand, in the sample S3 with 25% processing rate, the plateau region R2 disappeared, and additionally the strain leading to the breaking point BP (breaking elongation) decreased compared to the sample S1 without pressing. In the sample S4 with 40% processing rate, the plateau region R2 disappeared, and additionally the strain leading to the breaking point BP (breaking elongation) further decreased compared to the sample S1 without pressing. The above results elucidated that pressing of the distal end portion 11 of the first core shaft 10 made it possible to eliminate or reduce the superelasticity of the distal end portion 11 and decrease the strain leading to the breaking point BP (i.e., the breaking elongation can be shortened). In other words, the "elongation" of the distal end portion 11 caused by the superelasticity of the distal end portion 11 may be prevented by pressing the distal end portion 11 of the first core shaft 10.

Although not illustrated in FIG. 6, in the second core shaft 30, an amount of change in the strain (%) attributed to the large increase in the tensile load [N] in the region R1 is relatively small, compared to the samples S1 to S4 of the first core shaft.

Thus, in the samples S3 or S4 with pressing, change in the strain amount [%] leading to the breaking attributed to the tensile load [N] is closer to change in the strain amount [%] leading to the breaking attributed to the tensile load [N] of the second core shaft 30, compared to the sample S1 without pressing or the sample S2 with a low degree of pressing.

Figure 7:
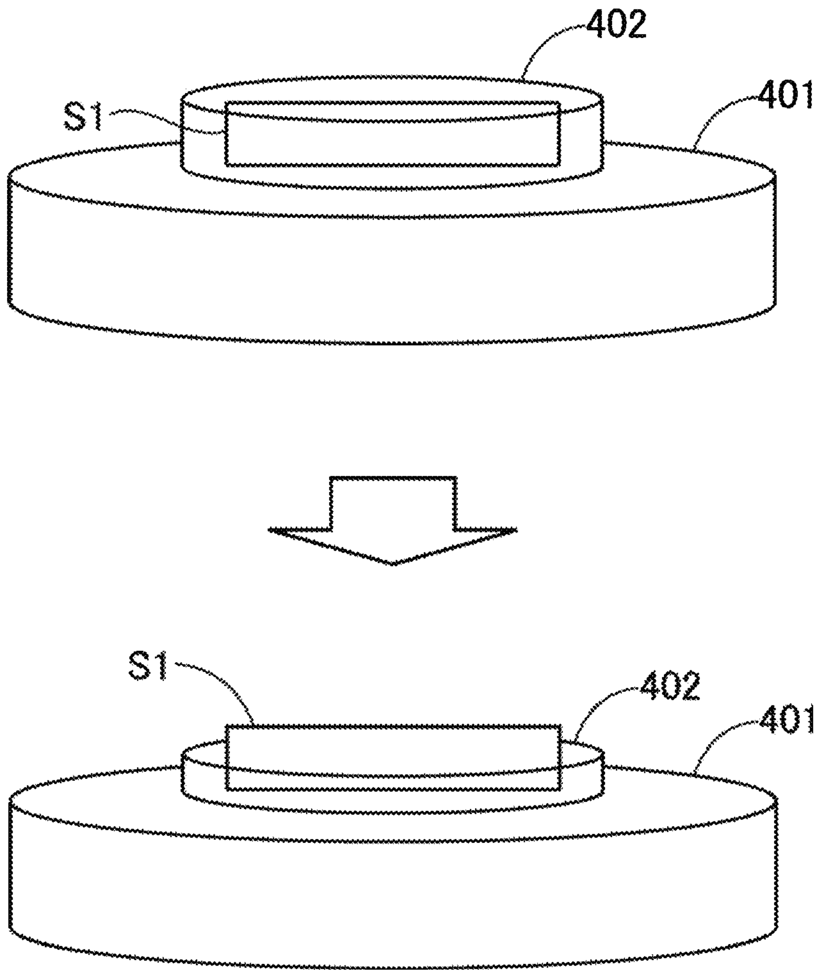
FIG. 7 illustrates a configuration of the sample of the first core shaft used for measuring a hardness.
Figure 8:
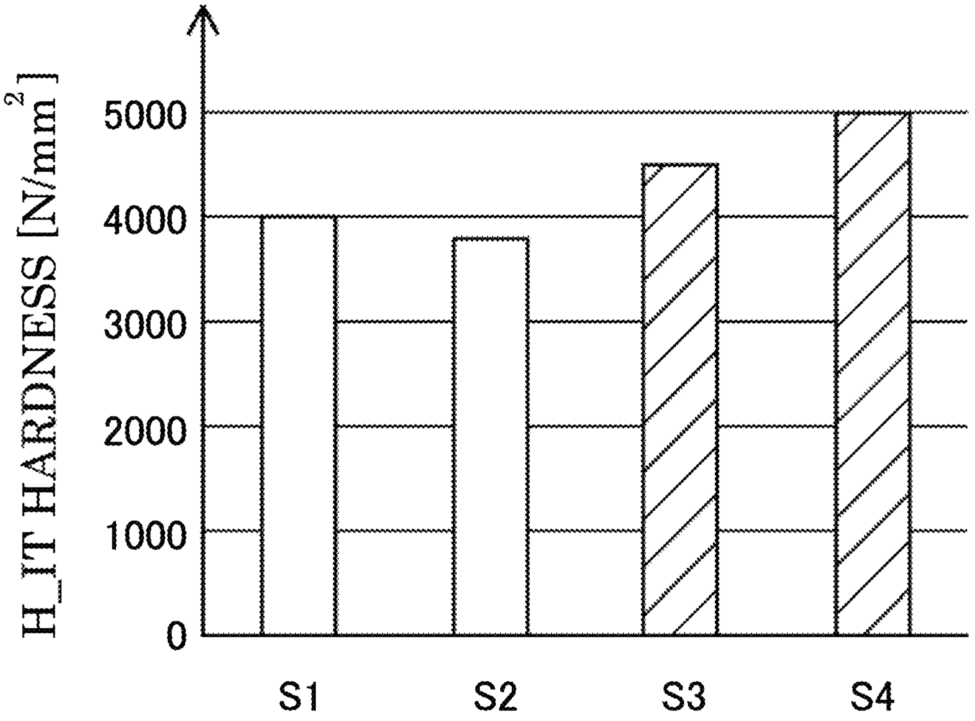
FIG. 8 is illustrates results of the hardness measurement.

With reference to FIG. 7 to FIG. 8, the relationship between the superelasticity and the nanoindentation hardness on the distal end portion 11 of the first core shaft 10 will be explained. Herein, the nanoindentation hardness of the four first core shaft samples S1 to S4 (FIG. 4) including the first core shaft with the configuration according to the first embodiment was measured, and the correlation between the measured hardness and the superelasticity was verified.

FIG. 7 illustrates a configuration of the sample of the first core shaft used for the hardness measurement. Four test specimens using the four samples S1 to S4 explained in FIG. 4 are prepared. The preparation of the test specimen using the sample S1 will be explained below. First, the sample S1 covered with a UV-curable adhesive 402 is placed on a pedestal 401 (FIG. 7: upper part). Next, the sample S1 placed on the pedestal 401 is crimped using a precision vise to remove air bubbles around the sample S1. Subsequently, the sample S1 placed on the pedestal 401 is irradiated with UV to harden the UV-curable adhesive 402. Then, the UV-curable adhesive 402 on the surface of the sample S1 is removed using a buffing grindstone and a diamond abrasive grain with 1 μm diameter (FIG. 7: lower part). In this way, the test specimen illustrated in the lower part of FIG. 7 is prepared for each of the samples S1 to S4.

A hardness measuring method will be explained. The hardness measurement was conducted using an ultrafine indentation hardness tester ENT-1100b and a Berkovich indenter manufactured by ELIONIX INC. In this measurement, an indentation load of the indenter was set to 100 mN, and the indentation speed was set to 10 mN/sec.

FIG. 8 illustrates results of the hardness measurement. In FIG. 8, the nanoindentation (H_IT) hardness ($N/mm^2$) for the samples S1 to S4 is plotted on the ordinate. As illustrated in the figure, the sample S1 had a nanoindentation hardness of 4000 $N/mm^2$, the sample S2 had a nanoindentation hardness of 3800 $N/mm^2$, the sample S3 had a nanoindentation hardness of 4500 $N/mm^2$, and the sample S4 had a nanoindentation hardness of 5000 $N/mm^2$. In FIG. 8, the samples S1 and S2 that did not show good results in the tensile test are represented by white bars, and the samples S3 and S4 that showed good results are represented by hatched bars.

Figure 9:
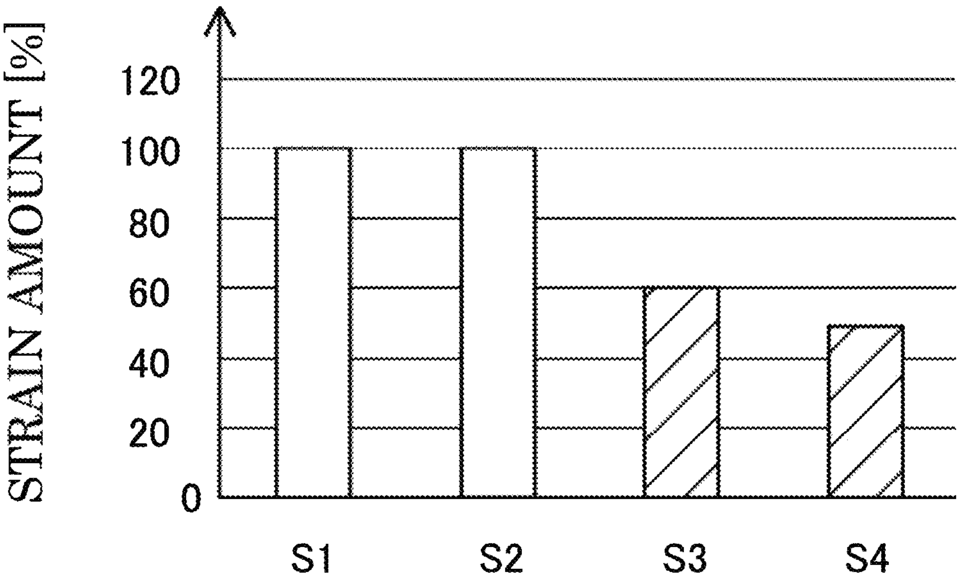
FIG. 9 illustrates strain amounts based on the measurement results.

FIG. 9 illustrates strain amounts based on the measurement results. FIG. 9 presents the tensile amounts obtained from the results of the tensile test (FIG. 6) for the samples S2 to S4 based on 100 of the strain amount of the sample S1 at the time of breaking. The strain amount of the sample S2 at the time of breaking point is substantially equal to that of the sample S1. The strain amount of the sample S3 is about 60% of the sample S1, and the strain amount of the sample S4 is about 50% of the sample S1.

As illustrated in FIG. 8 and FIG. 9, both the nanoindentation hardness (FIG. 8) and the strain amount at the time of breaking (FIG. 9) of the sample S2 with 8% processing rate did not greatly differ from those of the sample S1 without pressing. On the other hand, in the sample S3 with 25% processing rate, the nanoindentation hardness increased and the strain amount at the time of breaking decreased, compared to the sample S1 without pressing. In addition, in the sample S4 with 40% processing rate, the nanoindentation hardness further increased and the strain amount at the time of breaking further decreased, compared to the sample S1 without pressing. The above results elucidate that the strain amount leading to breaking decreased and the nanoindentation hardness increased by pressing the distal end portion 11 of the first core shaft 10.

The test results illustrated in FIG. 8 indicate that the nanoindentation hardness of the distal end portion 11 of the first core shaft 10 may be 4500 $N/mm^2$, which is the same as of the sample S3, or may be higher than 4500 $N/mm^2$. It is understood that the nanoindentation hardness of the distal end portion 11 of the first core shaft 10 may be 1.1 times or higher than the nanoindentation hardness of the portions (first reduced diameter portion 12, first large diameter portion 15, second reduced diameter portion 16, and second large diameter portion 17) on the proximal end side with respect to the distal end portion 11.

Figure 10:
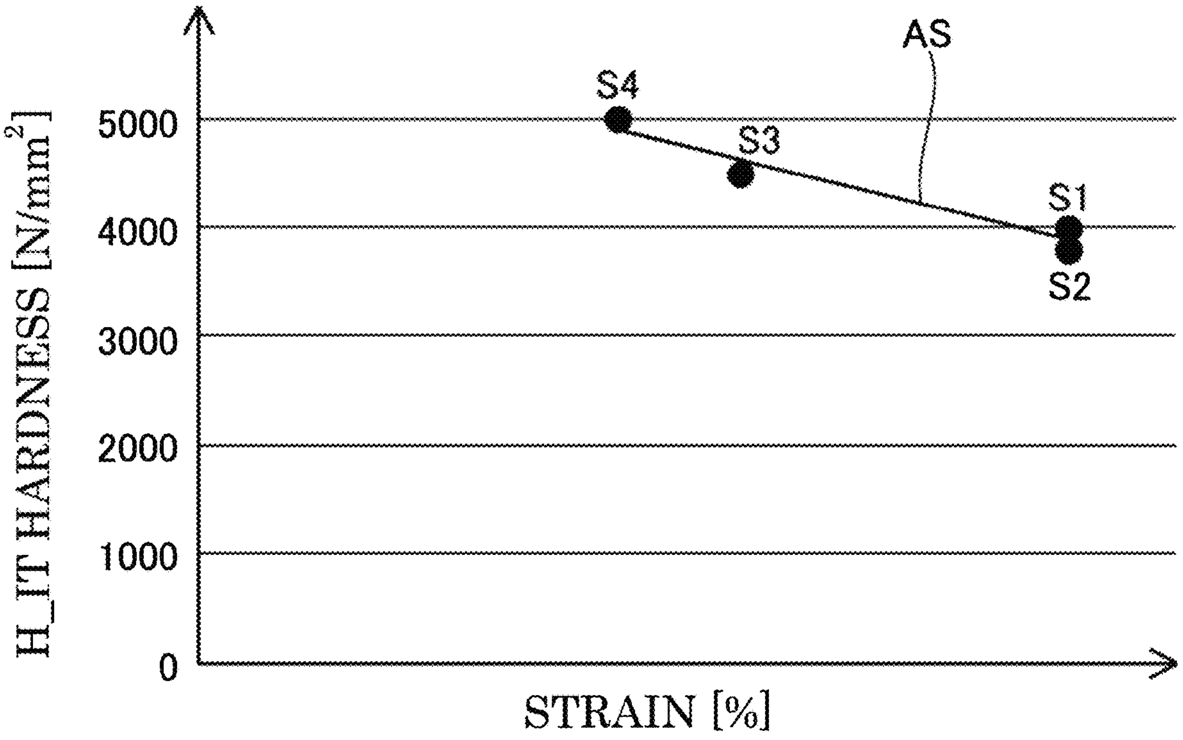
FIG. 10 illustrates a correlation between the hardness and a superelasticity.

FIG. 10 illustrates a correlation between the hardness and the superelasticity. FIG. 10 presents test results of the samples S1 to S4, in which the hardness measurement results ($N/mm^2$) are plotted on the ordinate and the tensile test results (strain leading to the breaking point BP, breaking elongation: %) are plotted on the abscissa. As illustrated in FIG. 10, as the test results for the samples S1 to S4, a linear approximation curve AS can be drawn. Thus, there is a strong correlation between the nanoindentation hardness and the strain leading to the breaking point BP (breaking elongation).

Second Embodiment

Figure 11:
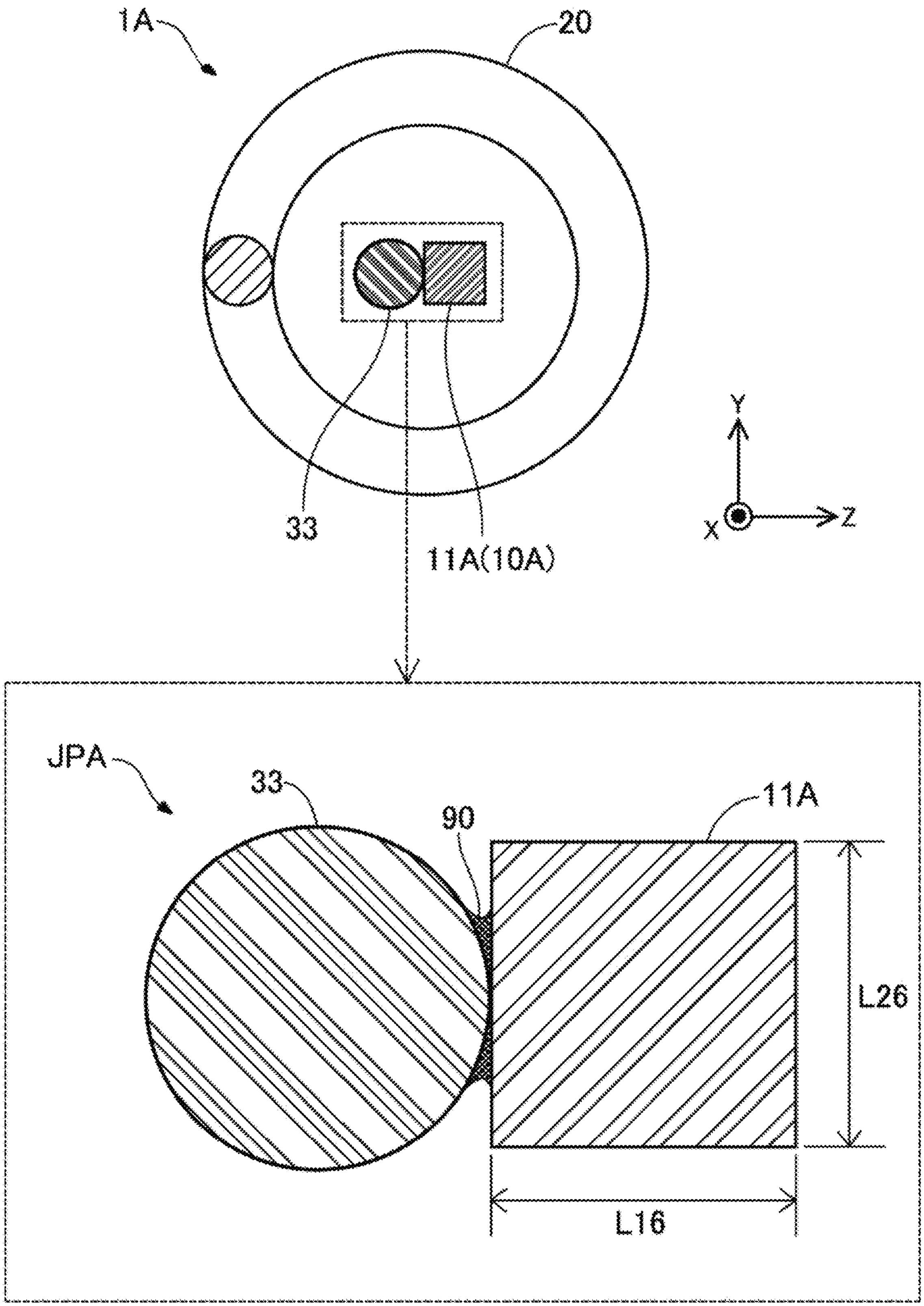
FIG. 11 is a transverse sectional view of a distal end side of a guide wire according to the second embodiment.

FIG. 11 is a transverse sectional view of a distal end side of a guide wire 1A according to the second embodiment. The guide wire 1A according to the second embodiment includes a first core shaft 10A instead of the first core shaft 10 according to the first embodiment. The first core shaft 10A includes a distal end portion 11A that has an almost square transverse section by being pressed from two directions. In other words, a width L16 and a height L26 of the distal end portion 11A may be substantially equal. To form the distal end portion 11A, the distal end portion 11 of the first core shaft 10 made of a superelastic material is pressed from both directions, the Z-axis direction and the Y-axis direction. The pressing allows the distal end portion 11A to have the same nanoindentation hardness as of the distal end portion 11 according to the first embodiment. That means, also in the first core shaft 10A according to the second embodiment, a superelasticity of the superelastic material can be eliminated or reduced on the distal end portion 11A to which the second core shaft 30 is joined.

In this way, the distal end portion 11A of the first core shaft 10A may have an almost polygonal transverse section such as an almost square shape and an almost rectangular shape. This guide wire 1A according to the second embodiment can also exhibit a similar effect to the first embodiment. Furthermore, in the guide wire 1A according to the second embodiment, an area of a part where the first core shaft 10A and the second core shaft 30 are adjacent to each other can be enlarged, so that a joining strength between the first core shaft 10A and the second core shaft 30 can be improved. The pressing is not necessarily performed from two directions, and may be performed from multiple directions.

Third Embodiment

Figure 12:
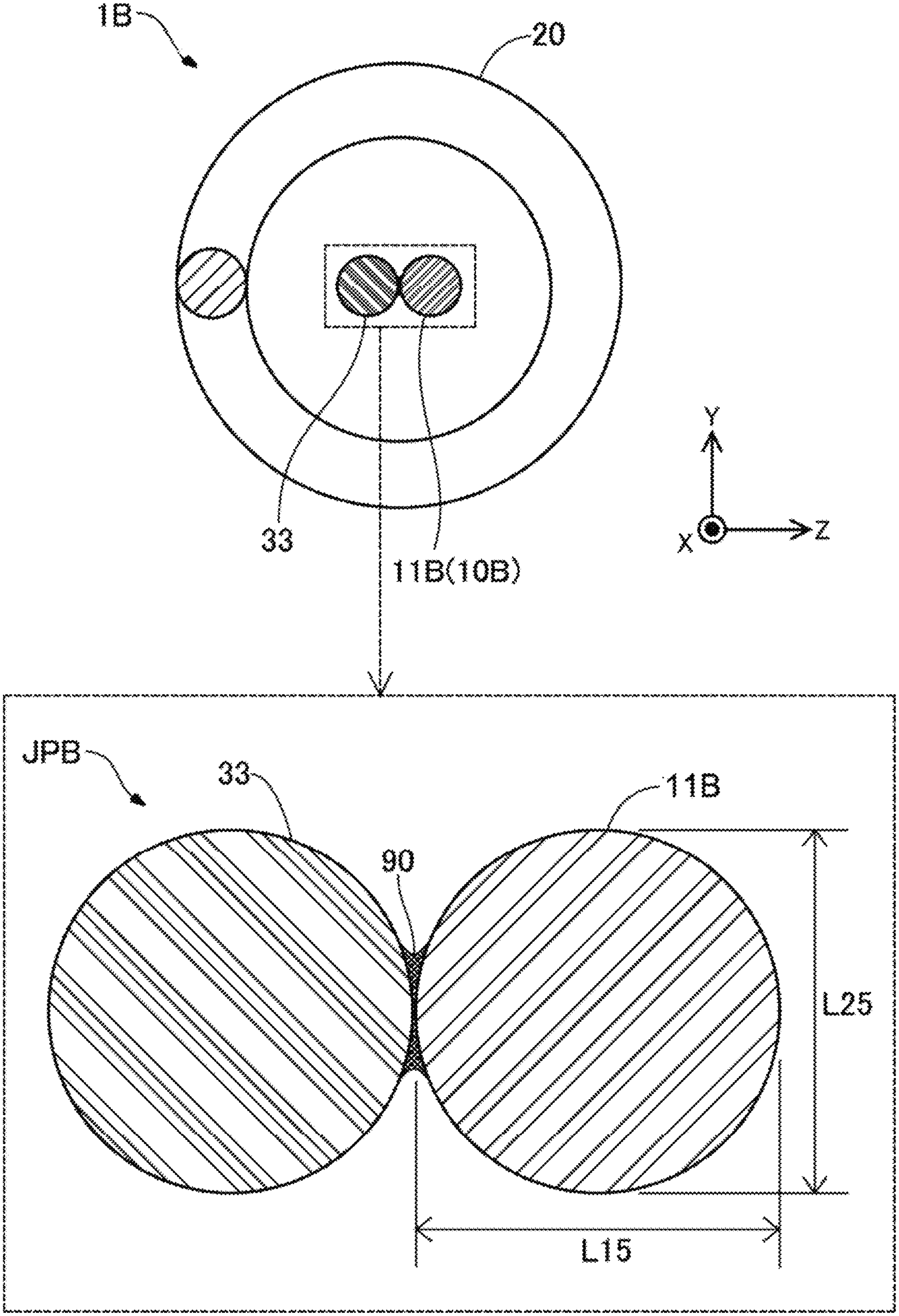
FIG. 12 is a transverse sectional view of a distal end side of a guide wire according to the third embodiment.

FIG. 12 is a transverse sectional view of a distal end side of a guide wire 1B according to the third embodiment. The guide wire 1B according to the third embodiment includes a first core shaft 10B instead of the first core shaft 10 according to the first embodiment. The first core shaft 10B includes a distal end portion 11B having an almost circular transverse section. In other words, a width L15 and a height L25 of the distal end portion 11B may be substantially equal. The distal end portion 11B is formed by swaging or drawing the distal end portion 11B of the first core shaft 10B made of a superelastic material. The swaging or drawing allow the distal end portion 11B to have the same nanoindentation hardness as of the distal end portion 11 according to the first embodiment. That means, also in the first core shaft 10B according to the third embodiment, a superelasticity of the superelastic material can be eliminated or reduced on the distal end portion 11B to which the second core shaft 30 is joined.

Thus, the distal end portion 11B of the first core shaft 10B may have an almost perfectly circular transverse sectional shape, and a high nanoindentation hardness, by swaging or drawing. In this case, the first reduced diameter portion 12 may be decreased in diameter toward the distal end by swaging or drawing to form the distal end portion 11B. This guide wire 1B according to the third embodiment can also exhibit a similar effect to the first embodiment. Furthermore, in the guide wire 1B according to the third embodiment, a processing rate of the first reduced diameter portion 12 gradually increases from the proximal end side toward the distal end side, so that a breaking elongation gradually decreases and the nanoindentation hardness gradually increases on the distal end portion 11B.

Fourth Embodiment

Figure 13:
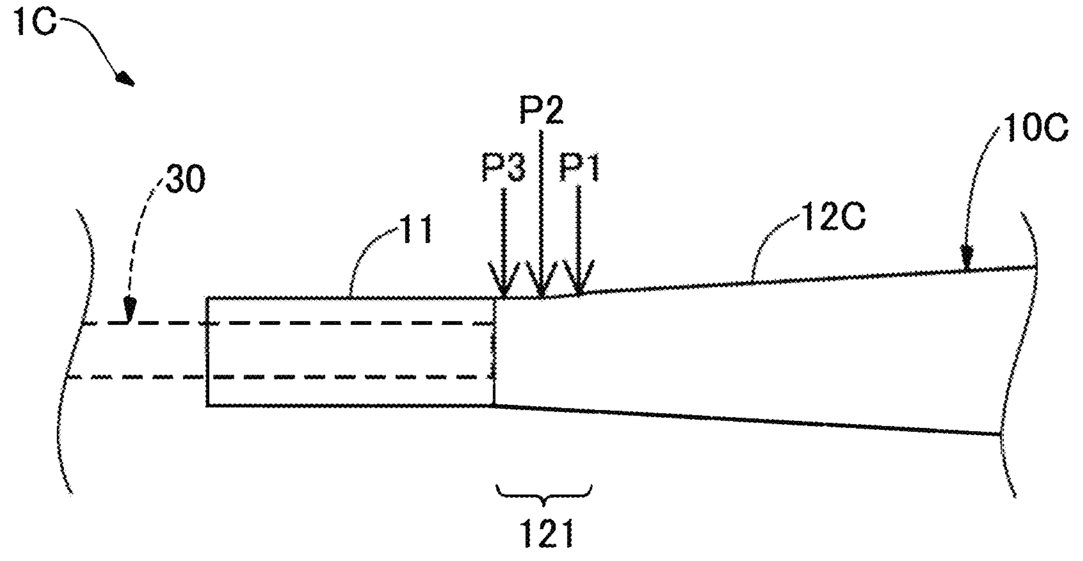
FIG. 13 illustrates a configuration of a distal end side of a first core shaft according to the fourth embodiment.

FIG. 13 illustrates a configuration of a distal end side of a first core shaft 10C according to the fourth embodiment. A guide wire 1C according to the fourth embodiment includes the first core shaft 10C instead of the first core shaft 10 according to the first embodiment. The first core shaft 10C includes a first reduced diameter portion 12C where a gradually-changed portion 121 is formed on the distal end portion. On the gradually-changed portion 121, the nanoindentation hardness gradually increases from the proximal end side toward the distal end side. When comparing the respective nanoindentation hardness of a proximal end-side portion P1, a middle portion P2, a distal end-side portion P3 of the gradually-changed portion 121, and the distal end portion 11, their nanoindentation hardness can be represented by proximal end-side portion P1<middle portion P2<distal end-side portion P3<distal end portion 11. When the first core shaft 10*a* is pressed, the distal end portion of the first reduced diameter portion 12C is clamped by an end portion of a jig to form the gradually-changed portion 121. The gradually-changed portion 121 may be formed using a jig with R on an end corner.

Thus, the configuration of the first core shaft 10C can be variously modified, and the first core shaft 10C may include the first reduced diameter portion 12C having the gradually-changed portion 121. A range (length in the axis line O direction) where the gradually-changed portion 121 is formed can be arbitrarily determined, and the gradually-changed portion 121 may not be a part on the distal end side explained in FIG. 13, but may be the entirety of the first reduced diameter portion 12C. This guide wire 1C according to the fourth embodiment can also exhibit a similar effect to the first embodiment. Furthermore, in the guide wire 1C according to the fourth embodiment, the gradually-changed portion 121 whose nanoindentation hardness gradually increases from the proximal end side toward the distal end side is provided on the distal end portion of the first reduced diameter portion 12C. Thereby, the superelasticity of the first core shaft 10C can be gradually decreased on the gradually-changed portion 121.

Fifth Embodiment

Figure 14:
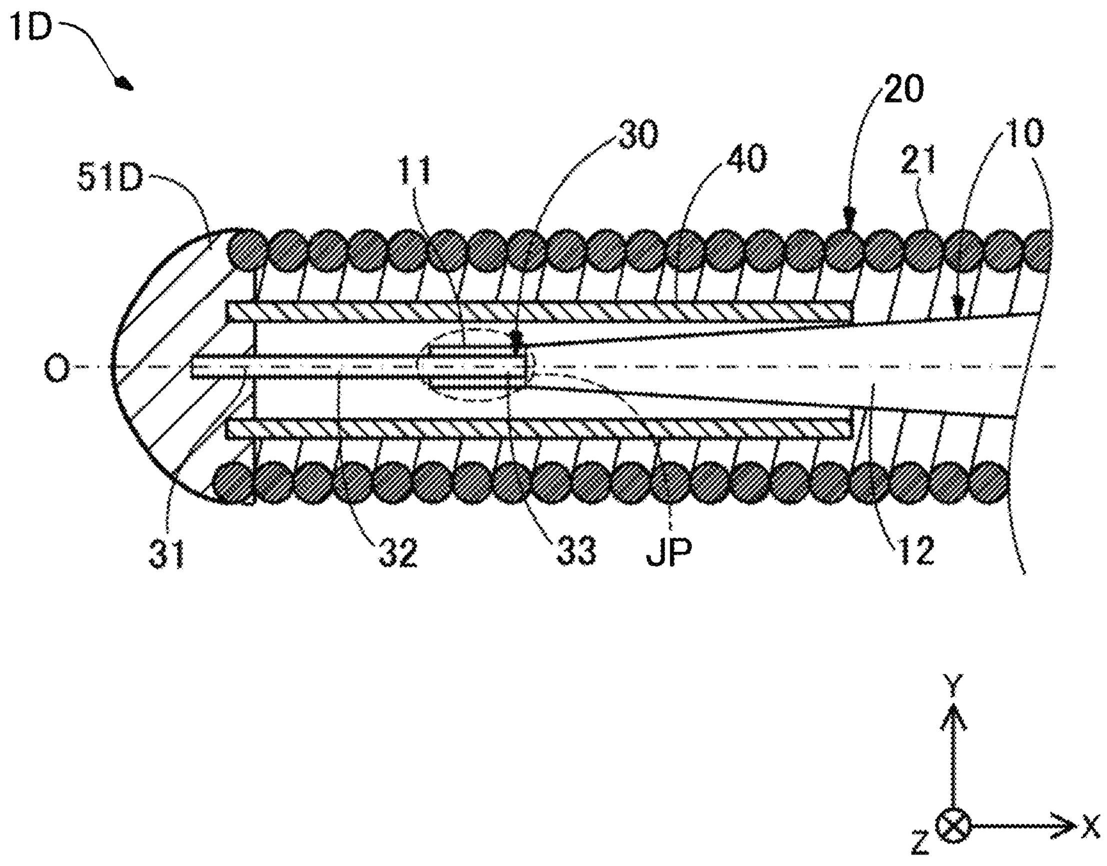
FIG. 14 illustrates a configuration of a distal end side of a guide wire according to the fifth embodiment.

FIG. 14 illustrates a configuration of a distal end side of a guide wire 1D according to the fifth embodiment. The guide wire 1D according to the fifth embodiment includes a covering portion 40. A distal fixation portion 51D integrally holds the distal end portion 31 of the second core shaft 30, the distal end portion of the core coil body 20, and the covering portion 40.

The covering portion 40 may be a single-thread coil formed using one wire, or a multi-thread coil formed by winding a plurality (e.g., eight) of wires in a multi-thread pattern, or a tubular member made of a resin or a metal formed into a tubular shape.

Sixth Embodiment

Figure 15:
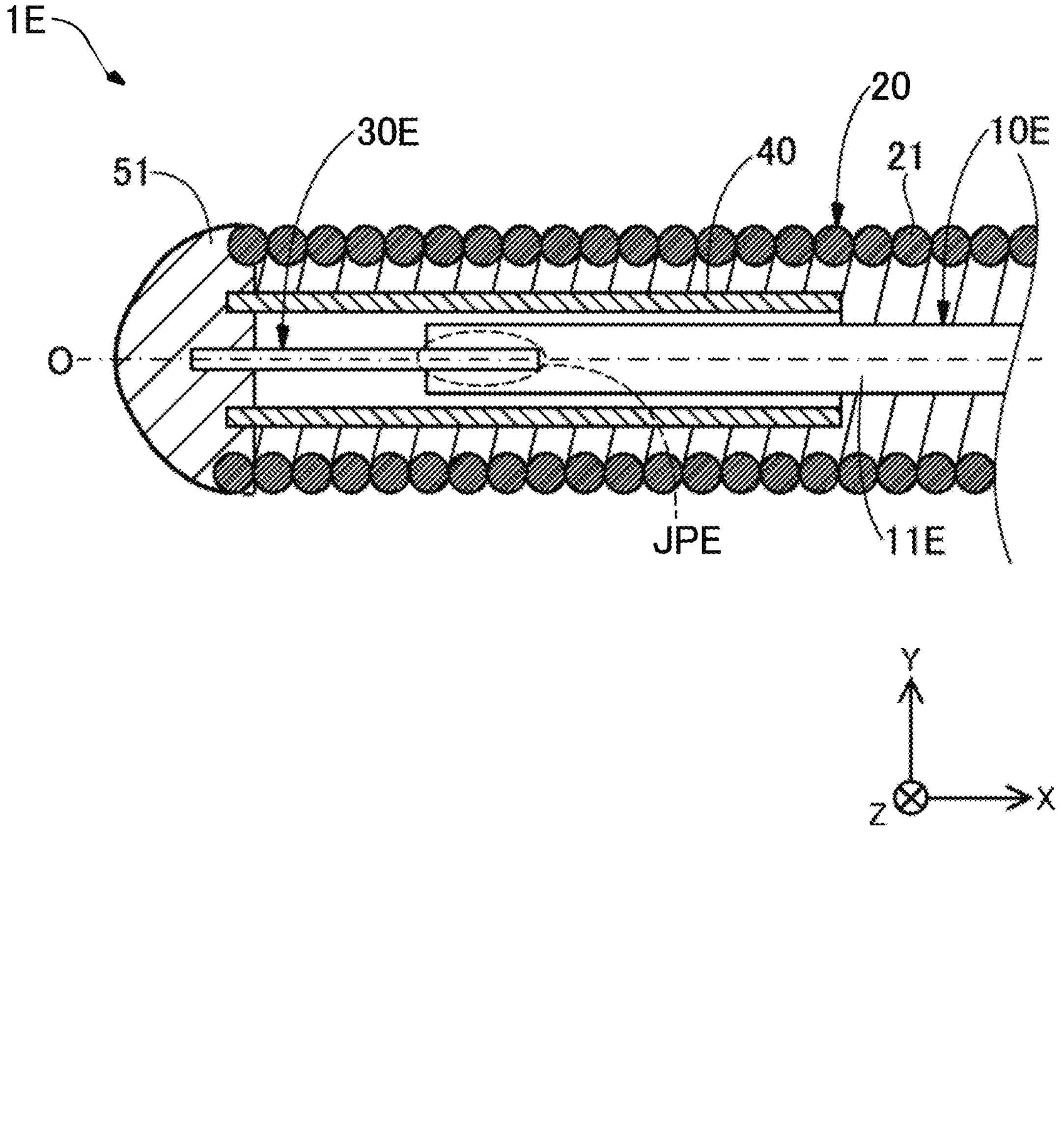
FIG. 15 is illustrates a configuration of a distal end side of a guide wire according to the sixth embodiment.

FIG. 15 illustrates a configuration of a distal end side of a guide wire 1E according to the sixth embodiment. The guide wire 1E according to the sixth embodiment include a first core shaft 10E instead of the first core shaft 10 explained in the first embodiment, a second core shaft 30E instead of the second core shaft 30, and the covering portion 40 explained in the fifth embodiment.

The first core shaft 10E does not include the distal end portion 11, the first reduced diameter portion 12, the first large diameter portion 15, the second reduced diameter portion 16, and the second large diameter portion 17 explained in the first embodiment, but has an almost cylindrical shape with a substantially constant outer diameter throughout the axial line O direction. In the first core shaft 10E, the distal end portion to which the second core shaft 30E is joined has a higher nanoindentation hardness and a smaller strain amount leading to the breaking, compared to the portions on the proximal end side with respect to the distal end portion. The nanoindentation hardness and the strain amount leading to the breaking on the distal end portion of the first core shaft 10E can be adjusted, e.g., by the aforementioned pressing. The second core shaft 30E does not include the distal end portion 31, the intermediate portion 32, and the proximal end portion 33 explained in the first embodiment, but has an almost cylindrical shape with a substantially constant outer diameter throughout the axial line O direction.

As described above, a configuration of at least one of the first core shaft 10E and the second core shaft 30E can be variously changed, and at least a part of each of the aforementioned portions (distal end portion 11, first reduced diameter portion 12, first large diameter portion 15, second reduced diameter portion 16, second large diameter portion 17, distal end portion 31, intermediate portion 32, and proximal end portion 33) may be omitted. This guide wire 1E according to the sixth embodiment can also exhibit a similar effect to the first embodiment.

Seventh Embodiment

Figure 16:
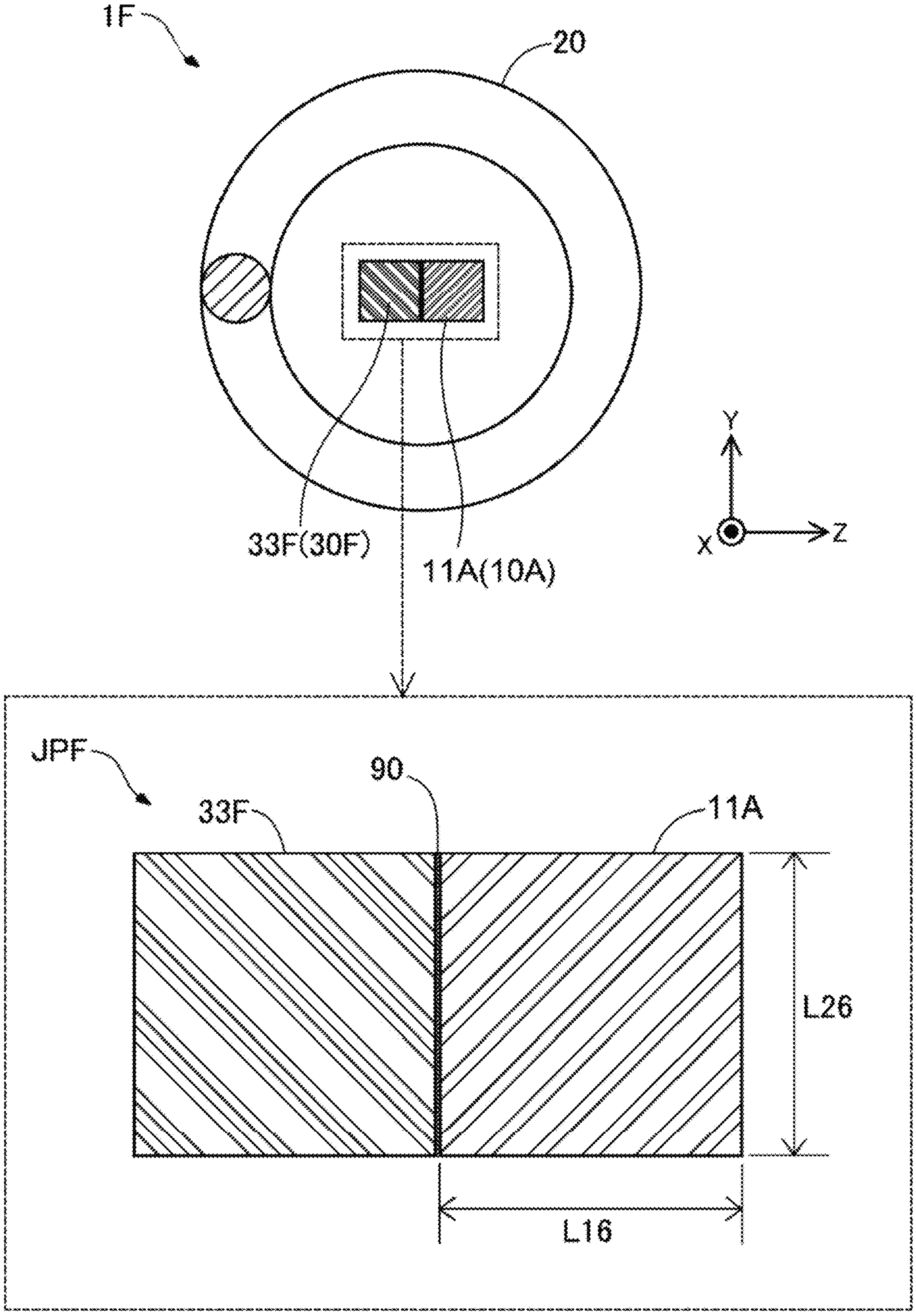
FIG. 16 is a transverse sectional view of a distal end side of a guide wire according to the seventh embodiment.

FIG. 16 is a transverse sectional view of a distal end side of a guide wire 1F according to the seventh embodiment. A guide wire 1F according to the seventh embodiment includes a second core shaft 30F instead of the second core shaft 30 according to the third embodiment. The second core shaft 30F includes a proximal end portion 33F having an almost square transverse section. To form the proximal end portion 33F, a proximal end portion 33*a* of a second core shaft 30*a* made of a material that is more plastically deformable than the first core shaft 10B is pressed from both the Z-axis direction and the Y-axis direction.

As described above, the configuration of the second core shaft 30F can be variously modified, and at least a part of the distal end portion 31, the intermediate portion 32, and the proximal end portion 33F may have an almost polygonal transverse section, such as an almost square shape and an almost rectangular shape. This guide wire 1F according to the seventh embodiment can also exhibit a similar effect to the first embodiment. Furthermore, in the guide wire 1F according to the seventh embodiment, an area of a part where the first core shaft 10B and the second core shaft 30F are adjacent to each other can be enlarged, so that a joining strength between the first core shaft 10B and the second core shaft 30F can be improved.

MODIFICATION EXAMPLES OF EMBODIMENTS

The disclosed embodiments are not limited to the above embodiments, and may be implemented in various modes without departing from the gist of the disclosed embodiments. For example, the following modifications can also be applied.

Modification Example 1

In the first to seventh embodiments, the configurations of the guide wires 1 and 1A to 1F have been illustrated. However, the configuration of the guide wire can be variously modified. For example, the guide wires according to the above embodiments have been explained as medical appliances used for inserting a catheter into a blood vessel, but the guide wire may be configured to be inserted into various organs in a human body, such as a lymphatic system, a biliary system, a urinary system, a respiratory system, a digestive system, a secretory gland, and a reproductive organ. For example, the guide wire may be configured such that the whole first core shaft is covered with the coil body without the second reduced diameter portion and the second large diameter portion. For example, the guide wire may be productized such that the distal end side is previously curved.

Modification Example 2

In the above first to seventh embodiments, the configurations of the first core shafts 10 and 10A to 10C, 10E and the configurations of the second core shafts 30, 30E, and 30F were illustrated. However, the configurations of the first and second core shafts can be variously modified. For example, the nanoindentation hardness on the distal end portion of the first core shaft may be not less than 1 time and less than 1.1 times the nanoindentation hardness of the portions on the proximal end side with respect to the distal end portion. This configuration also makes it possible to reduce the superelasticity of the distal end portion of the first core shaft by the difference in the nanoindentation hardness, so that the detachment destruction of the joint part caused by a load on the guide wire can be prevented. In addition, for example, the distal end portion of the first core shaft may have a nanoindentation hardness of lower than 4500 $N/mm^2$.

For example, the distal end portion of the first core shaft may have an almost truncated cone shape, similarly to the first reduced diameter portion. For example, the distal end portion of the first core shaft may be pressed. For example, the first core shaft may be formed by joining a plurality of members having different nanoindentation hardness. In this case, the pressing on the distal end portion of the first core shaft may be omitted.

For example, the proximal end portion of the second core shaft may be pressed only in one direction (e.g., Z-axis direction) to have an almost elliptical transverse section similarly to the distal end portion of the first core shaft according to the first embodiment. For example, in the joint part JP (FIG. 3, etc.), the first core shaft and the second core shaft may be disposed adjacent to each other not in the Z-axis direction explained in FIG. 3 and the like, but in the Y-axis direction. For example, on the joint part JP (FIG. 3, etc.), the arrangement of the first and second core shafts may be reversed.

Modification Example 3

In the aforementioned first to seventh embodiments, some examples of the configuration of the coil body 20 have been described. However, the configurations of the coil body can be variously modified. For example, the coil body may have a dense winding configuration with no gap between adjacent wires, a coarse winding configuration with gaps between adjacent wires, or a configuration in which the dense winding and the coarse winding are combined. The coil body may, for example, have a resin layer coated with a hydrophobic resin material, a hydrophilic resin material, or a mixture thereof. For example, the wire of the coil body does not necessarily have an almost circular transverse sectional shape.

Modification Example 4

The configurations of the guide wires 1 and 1A to 1F according to the first to seventh embodiments, and the configurations of the guide wires according to the modification examples 1 to 3 may be appropriately combined. For example, the guide wire may be configured by combining the second core shaft explained in the seventh embodiment (an example with an almost polygonal transverse section) and the first core shaft explained in the second, third, and fourth embodiments. For example, the guide wire may be configured by combining the second core shaft explained in the sixth embodiment (an example without distal end portion, intermediate portion, and proximal end portion) and the first core shaft explained in the first, second, third, and fourth embodiments. For example, the guide wire may be configured by combining the first core shaft explained in the sixth embodiment (an example without distal end portion, first reduced diameter portion, first large diameter portion, second reduced diameter portion, second large diameter portion) and the second core shaft explained in the first and seventh embodiments.

In the first to seventh embodiments, although the first core shaft 10 is disposed up to the proximal end portion, a third core shaft made of SUS or the like may be disposed on the proximal end side of the first core shaft 10. In such a configuration, the nanoindentation hardness and the strain amounts leading to breaking of the distal end portions 11, 11A, and 11B of the first core shaft 10 should be compared in a range where the first core shaft 10 is disposed.

Although the aspects of the disclosed embodiments have been explained above based on the embodiments and the modification examples, the embodiments of the aforementioned aspects are made for facilitating understanding of the aspects, and do not limit the aspects. The aspects can be modified and improved without departing from the spirit of the aspects and the scope of claims, and the aspects include equivalents thereof. Further, unless the technical features are described as essential in the present specification, the technical features may be omitted as appropriate.

DESCRIPTION OF REFERENCE NUMERALS

1, 1A to 1F Guide wire
10, 10A to 10C, 10E First core shaft
11, 11A, 11B Distal end portion
12, 12C First reduced diameter portion
15 First large diameter portion
16 Second reduced diameter portion
17 Second large diameter portion
20 Coil body
21 Wire
30, 30E, 30F Second core shaft
31 Distal end portion
32 Intermediate portion
33, 33F Proximal end portion
40 Covering portion
51, 51D Distal fixation portion
52 Proximal fixation portion
61 Intermediate fixation portion
90 Joining agent
111, 112, 113, 114 Distal end portion
121 Gradually-changed portion
201 First chuck
202 Second chuck
301, 302 Solder agent
401 Pedestal
402 UV-curable adhesive

What is claimed is:

1. A guide wire comprising:

a first core shaft made of a superelastic material; and a second core shaft made of a material more plastically deformable than the first core shaft and joined to a distal end portion of the first core shaft, wherein on the distal end portion to which the second core shaft is joined in the first core shaft, a breaking elongation attributed to a tensile load is lesser compared to a portion on a proximal end side of the first core shaft with respect to the distal end portion, a difference between a breaking elongation attributed to a tensile load on the distal end portion of the first core shaft and a breaking elongation attributed to a tensile load on the second core shaft is smaller than a difference between a breaking elongation attributed to a tensile load on the proximal end side of a portion of the first core shaft and the breaking elongation attributed to the tensile load on the second core shaft, the first core shaft has a reduced diameter portion whose outer diameter decreases from the proximal end side toward a distal end side of the guide wire, the second core shaft does not overlap the reduced diameter portion of the first core shaft, and a proximal end of the second core shaft is located further toward the distal end side of the guide wire than a distal end of the reduced diameter portion of the first core shaft.

2. The guide wire according to claim 1, wherein a nanoindentation hardness on the distal end portion of the first core shaft is higher compared to the portion on the proximal end side with respect to the distal end portion.

3. The guide wire according to claim 2, wherein the nanoindentation hardness on the distal end portion of the first core shaft is not less than 1.1 times the nanoindentation hardness of the portion on the proximal end side with respect to the distal end portion.

4. The guide wire according to claim 3, wherein the nanoindentation hardness on the distal end portion of the first core shaft is 4500 $N/mm^2$ or higher.

5. The guide wire according to claim 4, wherein the distal end portion of the first core shaft is connected to a distal end of the reduced diameter portion.

6. The guide wire according to claim 5, further comprising:

a portion having a nanoindentation hardness that increases from the proximal end side toward the distal end side on the distal end portion of the reduced diameter portion.

7. The guide wire according to claim 3, wherein the distal end portion of the first core shaft is connected to a distal end of the reduced diameter portion.

8. The guide wire according to claim 7, further comprising:

a portion having a nanoindentation hardness that increases from the proximal end side toward the distal end side on the distal end portion of the reduced diameter portion.

9. The guide wire according to claim 2, wherein the nanoindentation hardness on the distal end portion of the first core shaft is 4500 $N/mm^2$ or higher.

10. The guide wire according to claim 9, wherein the distal end portion of the first core shaft is connected to a distal end of the reduced diameter portion.

11. The guide wire according to claim 10, further comprising:

a portion having a nanoindentation hardness that increases from the proximal end side toward the distal end side on the distal end portion of the reduced diameter portion.

12. The guide wire according to claim 2, wherein the distal end portion of the first core shaft is connected to a distal end of the reduced diameter portion.

13. The guide wire according to claim 12, further comprising:

a portion having a nanoindentation hardness that increases from the proximal end side toward the distal end side on the distal end portion of the reduced diameter portion.

14. The guide wire according to claim 1, wherein the distal end portion of the first core shaft is connected to a distal end of the reduced diameter portion.

15. The guide wire according to claim 14, further comprising:

a portion having a nanoindentation hardness that increases from the proximal end side toward the distal end side on the distal end portion of the reduced diameter portion.

16. The guide wire according to claim 14, further comprising:

a coil body that covers at least a distal end side of the first core shaft, and the second core shaft; and a covering portion disposed inside the coil body and covering a joint part between the first core shaft and the second core shaft, wherein the covering portion covers, in addition to the joint part, a distal end side of the reduced diameter portion of the first core shaft.

17. The guide wire according to claim 1, wherein on the distal end portion of the first core shaft, a plateau region of the superelastic material is eliminated.

18. The guide wire according to claim 1, further comprising:

a coil body that covers at least a distal end side of the first core shaft, and the second core shaft; and a covering portion disposed inside the coil body and covering a joint part between the first core shaft and the second core shaft.

19. The guide wire according to claim 1, wherein in the second core shaft, a portion adjacent to the distal end portion of the first core shaft is entirely joined.

20. The guide wire according to claim 1, wherein the distal end portion of the first core shaft has a non-circular transverse cross-section, and a longitudinal lateral face of the distal end portion is adjacent to the second core shaft.

21. The guide wire according to claim 20, wherein the distal end portion of the first core shaft has a polygonal transverse cross-section.

22. A method for manufacturing a guide wire, comprising:

subjecting a distal end portion of a first core shaft made of a superelastic material, to first processing using at least one of pressing, swaging, and drawing; and joining a second core shaft made of a material that is more plastically deformable than the first core shaft, to the distal end portion subjected to the first processing, wherein by the first processing, a breaking elongation attributed to a tensile load on the distal end portion of the first core shaft is lesser compared to a portion on a proximal end side of the first core shaft with respect to the distal end portion, a difference between a breaking elongation attributed to a tensile load on the distal end portion of the first core shaft and a breaking elongation attributed to a tensile load on the second core shaft is smaller than a difference between a breaking elongation attributed to a tensile load on the proximal end side of a portion of the first core shaft and the breaking elongation attributed to the tensile load on the second core shaft, the first core shaft has a reduced diameter portion whose outer diameter decreases from the proximal end side toward a distal end side of the guide wire, the second core shaft does not overlap the reduced diameter portion of the first core shaft, and a proximal end of the second core shaft is located further toward the distal end side of the guide wire than a distal end of the reduced diameter portion of the first core shaft.

* * * * *